(12) United States Patent
Manoharan

(10) Patent No.: US 6,169,177 B1
(45) Date of Patent: Jan. 2, 2001

(54) PROCESSES FOR THE SYNTHESIS OF OLIGOMERIC COMPOUNDS

(75) Inventor: Muthiah Manoharan, Carlsbad, CA (US)

(73) Assignee: Isis Pharmaceuticals, Inc., Carlsbad, CA (US)

( * ) Notice: Under 35 U.S.C. 154(b), the term of this patent shall be extended for 0 days.

(21) Appl. No.: 09/187,995

(22) Filed: Nov. 6, 1998

(51) Int. Cl.$^7$ .......................... C07H 21/00; C07H 21/02; C07H 21/04

(52) U.S. Cl. .................... 536/25.31; 536/25.33; 536/25.34

(58) Field of Search ............... 536/25.31, 25.33, 536/25.34

(56) References Cited

U.S. PATENT DOCUMENTS

| Re. 34,069 | 9/1992 | Köster et al. ............... 536/25.34 |
|---|---|---|
| 3,687,808 | 8/1972 | Merigan et al. ............. 435/91.3 |
| 4,415,732 | 11/1983 | Caruthers et al. ........... 536/26.5 |
| 4,458,066 | 7/1984 | Caruthers et al. ........... 536/25.34 |
| 4,500,707 | 2/1985 | Caruthers et al. ........... 536/25.34 |
| 4,668,777 | 5/1987 | Caruthers et al. ........... 536/26.5 |
| 4,725,677 | 2/1988 | Köster et al. .............. 536/25.34 |
| 4,816,571 | 3/1989 | Andrus et al. .............. 536/25.3 |
| 4,973,679 | 11/1990 | Caruthers et al. ........... 536/26.71 |
| 5,026,838 | 6/1991 | Nojiri et al. ............... 536/25.34 |
| 5,132,418 | 7/1992 | Caruthers et al. ........... 536/25.3 |
| 5,212,295 | 5/1993 | Cook ........................ 536/26.7 |
| 5,670,633 | 9/1997 | Cook et al. ................ 536/23.1 |

OTHER PUBLICATIONS

Alul, R.H. et al., "Oxalyl–CPG: a labile support for synthesis of sensitive oligonucleotide derivatives", *Nuc. Acid Res.*, 1991, 19, 1527–1532 (Issue No. 7), Month of publication data is unavailable for this reference.

Beaucage, S.L. et al., "Advances in the Synthesis of Oligonucleotides by the Phosphoramidite Approach", *Tetrahedron*, 1992, 48, 2223–2311 (Issue No., Month of publication data is unavailable for this reference.

Bergmann et al., "Allyl as Internucleotide Preotecting Group in DNA Synthesis to be Cleaved Off By Ammonia", *Tetrahedron*, 1995, 51(25), 6971–6976(Iss. No. 25), Month of publication data is unavailable for this reference.

Bielinska, A. et al., "Regulation of Gene Expression with Double–Stranded Phosphorothioate Oligonucleotides", *Science*, 1990, 250, 997–100 (Nov. 16, 1990).

Brown, T. et al., "Modern machine–aided methods of oligodeoxyribonucleotide synthesis", *Oligonucleotides and Analogs A Practical Approach*, 1991, Chapter 1, Ekstein, F., ed., IRL Press, Oxford, 1–24, Month of publication data is unavailable for this reference.

Cook, P.D., "Medicinal Chemistry of Antisense Oligonucleotides—future opportunities", *Anti–Cancer Drug Design*, 1991, 6, 585–607, Month of publication data is unavailable for this reference.

Davis et al., "Applications of Oxaziridines in Organic Synthesis", *Tetrahedron*, 1989, 45(18), 5703–5742, Month of publication data is unavailable for this reference.

Delgado, C. et al., "The Uses and Properties of PEG–Linked Proteins", *Crit. Rev. in Therapeutic Drug Carrier Sys.*, 1992, 9, 249–304 (Issue No. 3–4), Month of publication data is unavailable for this reference.

Efimov, V.A. et al., "New efficient sulfurizing reagents for the preparation of oligodeoxyribonucleotide phosphorothioate analogues", *Nucl. Acids Res.*, 1995, 23, 4029–4033 (Issue No. 20), Month of publication data is unavailable for this reference.

Englisch, U. et al., "Chemically Modified Oligonucleotides as Probes and Inhibitors", *Angew. Chem. Int. Ed. Eng.*, 1991, 30, 613–629 (Issue No. 6, Jun. 1991).

Greene, T. W. et al., "Protection for the Amino Group," *Protective Groups in Organic Synthesis*, 1991, Chapter 7, John Wiley & Sons, 309–405, Month of publication data is unavailable for this reference.

Greene, T. W. et al., "Protection for the Hydroxyl Group Including 1,2– And 1,3–Diols," *Protective Groups in Organic Synthesis*, 1991, Chapter 2, John Wiley & Sons, 10–142, Month of publication data is unavailable for this reference.

Hamm et al., "Incorporation of 2'–Deoxy–2'–mercaptocytidine into Oligonucleotides via Phosphoramidite Chemistry", *J. Org. Chem.*, 1997, 62(10), 3415–3420, Month of publication data is unavailable for this reference.

Hayakawa, Y. et al., "The Allylic Protection Method in Solid–Phase Oligonucleotide Synthesis. An Efficient Preparation of Solid–Anchored DNA Oligomers," *J. Am. Chem. Soc.*, 1990, 112, 1691–1696 (Issue No. 5), Month of publication data is unavailable for this reference.

Hayakawa et al., "O–Allyl Protection of Guanine and Thymine Residues in Oligodeoxyribonucleotides", *J. Org. Chem.*, 1993, 58(20), 5551–5555, Month of publication data is unavailable for this reference.

Hayakawa et al., "Electrochemical Removal of Allylic Protecting Groups in Nucleotide Synthesis", *Nucleosides & Nucleotides*, 1998, 17(1–3), 441–449, Month of publication data is unavailable for this reference.

(List continued on next page.)

*Primary Examiner*—Gary Geist
(74) *Attorney, Agent, or Firm*—Woodcock Washburn Kurtz Mackiewicz & Norris LLP

(57) ABSTRACT

The present invention provides synthetic processes by which oligomeric compounds, having at least one phosphodiester or phosphorothioate linkage, are prepared. The synthetic processes use a novel mixture of concentrated ammonium hydroxide and a thiol compound during the deblocking step of all or selected internucleoside linkages. Alternatively, the deblocking is carried out in two steps using a mercapto compound in an aqueous amine followed by concentrated ammonium hydroxide. Also provided are synthetic intermediates useful in such processes. Novel oxidation procedures to give phosphodiester oligomers are also included.

34 Claims, No Drawings

OTHER PUBLICATIONS

Hayakawa et al., "Allyl Protection in the Synthesis of Oligodeoxyribonucleotide Phosphorothioates", *Nucleosides & Nucleotides,* 1994, 13(6&7), 1337–1345, Month of publication data is unavailable for this reference.

Iyer, R.P. et al., "The Automated Synthesis of Sulfur–Containing Oligodeoxyribonucleotides Using 3H–1, 2–Benzodithiol–3–one 1,1–Dioxide as a Sulfur–Transfer Reagent", *J. Org. Chem.,* 1990, 55, 4693–4699 (Issue No. 15), Month of publication data is unavailable for this reference.

Iyer, R.P. et al., "3H–1,2–Benzodithiole–3–one 1,1–Dioxide as an Improved Sulfurizing Reagent in the Solid–Phase Synthesis of Oligodeoxyribonucleoside Phosphorothioates", *J. Am. Chem. Soc.,* 1990, 112, 1253–1254, Month of publication data is unavailable for this reference.

Kamer, P.C.J. et al., "An Efficient Approach Toward the Synthesis of Phosphorothioate Diesters via the Schonberg Reaction", *Tetrahedron Letts.,* 1989, 30, 6757–6760 (Issue No. 48), Month of publication data is unavailable for this reference.

Kroschwitz, J.I., "Polynucleotides", *Concise Encyclopedia of Polymer Science and Engineering,* 1990, John Wiley & Sons, New York, 858–859, Month of publication data is unavailable for this reference.

Ouchi, T. et al., "Synthesis and Antitumor Activity of Poly(Ethylene Glycol)s Linked to 5'–Fluorouracil via a Urethane or Urea Bond", *Drug Des. & Disc.,* 1992, 9, 93–105, Month of publication data is unavailable for this reference.

Polushin et al., "Synthesis of Oligonucleotides Containing 2'–Azido– and 2'–Amino–2'–deoxyuridine Using Phosphotriester Chemistry", *Tetrahedron Lett.,* 1996, 37(19), 3227–3230, Month of publication data is unavailable for this reference.

Rao, M.V. et al., "Dibenzoyl Tetrasulphide–A Rapid Sulphur Transfer Agent in the Synthesis of Phosphorothioate Analogues of Oligonucleotides", *Tetrahedron Letts.,* 1992, 33, 4839–4842 (Issue No. 33), Month of publication data is unavailable for this reference.

Ravasio, N. et al., "Selective Hydrogenations Promoted by Copper Catalysts. 1. Chemoselectivity, Regioselectivity, and Stereoselectivity in the Hydrogenation of 3–Substituted Steroids", *J. Org. Chem.,* 1991, 56, 4329–4333 (Issue No. 13), Month of publication data is unavailable for this reference.

Sanghvi, Y.S., "Heterocyclic Base Modifications in Nucleic acids and their Applications in Antisense Oligonucleotides", *Antisense Research and Applications,* 1993, Chapter 15, CRC Press, Boca Raton, 273–288, Month of publication data is unavailable for this reference.

Secrist, J.A. et al., "Synthesis and Biological Activity of 4'–Thionucleosides", 10*th International Rountable: Nucleosides, Nucleotides and their Biological Applications,* Sep. 16–20, 1992, Abstact 21, Park City, Utah, 40.

Stec, W.J. et al., "Bis(O,O–Diisopropoxy Phosphinothioyl) Disulfide—A Highly Efficient Sulfurizing Reagent for Cost–Effective Synthesis of Oligo(Nucleoside Phosphorothioate)s", *Tetrahedron Letts.,* 1993, 34, 5317–5320 (Iss. No. 33), Month of publication data is unavailable for this reference.

Thomson, J.B. et al., "Synthesis and Properties of Diuridine Phosphate Analogues Containing Thio and Amino Modifications",*J. Org. Chem.,* 1996, 61(18), 6273–6281, Month of publication data is unavailable for this reference.

Vu, H. et al., "Internucleotide Phosphite Sulfurization with Tetraethylthiuram Disulfide. Phosphorothioate Oligonucleotide Synthesis via Phosphoramidite Chemistry", *Tetrahedron Letts.,* 1991, 32, 3005–3008 (Issue No. 26), Month of publication data is unavailable for this reference.

Wright, P. et al., "Large Scale Synthesis of Oligonucleotides via phosphoramidite Nucleosides and a High–loaded Polystyrene Support", *Tetrahedron Letts.,* 1993, 34, 3373–3376 (Issue No. 21), Month of publication data is unavailable for this reference.

Wu, H. et al., "Inhibition of in vitro transcription by specific double–stranded oligodeoxyribonucleotides", *Gene,* 1990, 89, 203–209, Month of publication data is unavailable for this reference.

Xu, Q. et al., "Efficient introduction of phosphorothioates into RNA oligonucleotides by 3–ethoxy–1,2, 4–dithiazoline–5–one (EDITH)", *Nucl. Acids Res.,* 1996, 24, 3643–3644 (Issue No. 18), Month of publication data is unavailable for this reference.

Xu, Q. et al., "Use of 1,2,4–dithiazolidine (DtsNH) and 3–ethoxy–1,2,4–dithiazoline–5–one (EDITH) for synthesis of phosphorothioate–containing oligodeoxyribonucleotides", *Nucl. Acids Res.,* 1996, 24, 1602–1607 (Issue No. 9), Month of publication data is unavailable for this reference.

SEQUENCE LISTING

<160> NUMBER OF SEQ ID NOS: 13

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Novel Sequence

<400> SEQUENCE: 1 ttttttttttt tt                                                          12

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 2 ttttttttttt tt                                                          12

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 3
tgcatccccc aggccaccat                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 4
tgcatccccc aggccaccat                                                   20

<210> SEQ ID NO 5
<211> LENGTH: 5
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 5 gaact                                                                    5

<210> SEQ ID NO 6
<211> LENGTH: 5
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 6 gacct                                                                    5

<210> SEQ ID NO 7
<211> LENGTH: 5
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 7 gagct                                                              5

<210> SEQ ID NO 8
<211> LENGTH: 5
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 8 gaact                                                              5

<210> SEQ ID NO 9
<211> LENGTH: 5
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 9 gacct                                                              5

<210> SEQ ID NO 10
<211> LENGTH: 5
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 10 gagct                                                              5

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 11
gcccaagcta tccgtggcca                                             20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 12
gcccaagctg gcatccgtca                                             20

<210> SEQ ID NO 13
<211> LENGTH: 5
<212> TYPE: DNA
<213> ORGANISM: Artificial Sequence
<220> FEATURE:

```
<223> OTHER INFORMATION: Description of Artificial Sequence:  Novel
      Sequence

<400> SEQUENCE: 13 gtact                                                                        5
```

PROCESSES FOR THE SYNTHESIS OF OLIGOMERIC COMPOUNDS

FIELD OF THE INVENTION

This invention relates to methods for the preparation of oligomeric compounds, especially those having at least one phosphodiester or phosphorothioate linkage. The methods of the invention include the use of an allyl protecting group either at selected linkages or all linkages, followed by a novel deprotection strategy step using a mercapto compound in an aqueous amine or concentrated ammonium hydroxide to effect cleavage of the allyl protecting group.

BACKGROUND OF THE INVENTION

Oligonucleotides and their analogs have been developed and used in molecular biology in a variety of procedures as probes, primers, linkers, adapters, and gene fragments. Modifications to oligonucleotides used in these procedures include labeling with nonisotopic labels, e.g. fluorescein, biotin, digoxigenin, alkaline phosphatase, or other reporter molecules. Other modifications have been made to the ribose phosphate backbone to increase the nuclease stability of the resulting analog. Examples of such modifications include incorporation of methyl phosphonate, phosphorothioate, or phosphorodithioate linkages, and 2'-O-methyl ribose sugar units. Further modifications include those made to modulate uptake and cellular distribution. With the success of these compounds for both diagnostic and therapeutic uses, there exists an ongoing demand for improved oligonucleotides, their analogs and synthetic processes for their preparation.

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics has generally focused on interactions with such proteins in efforts to moderate their disease-causing or disease-potentiating functions. In newer therapeutic approaches, modulation of the actual production of such proteins is desired. By interfering with the production of proteins, maximum therapeutic effect may be obtained with minimal side effects. It is, therefore, a general object of such therapeutic approaches to interfere with or modulate gene expression which would otherwise lead to undesired protein formation.

One method for inhibiting specific gene expression involves using oligonucleotides, especially oligonucleotides which are complementary to a specific target messenger RNA (mRNA) sequence. Several oligonucleotides are currently undergoing clinical trials for such use. Phosphorothioate oligonucleotides are presently being used as such antisense agents in human clinical trials for various disease states, including use as antiviral agents.

Transcription factors interact with double-stranded DNA during regulation of transcription. Oligonucleotides can serve as competitive inhibitors of transcription factors to modulate their action. Several recent reports describe such interactions. See, Bielinska et. al., *Science*, 1990, 250, 997–1000; and Wu et. al., *Gene*, 1990, 89, 203–209.

In addition to their use as both indirect and direct regulators of protein production, oligonucleotides and their analogs have also found use in diagnostic tests. Such diagnostic tests can be performed using biological fluids, tissues, intact cells or isolated cellular components. As with inhibition of gene expression, diagnostic applications utilize the ability of oligonucleotides and their analogs to hybridize with a complementary strand of nucleic acid. Hybridization is the sequence-specific hydrogen bonding of oligomeric compounds, via Watson-Crick and/or Hoogsteen base pairs, to RNA or DNA. The bases of such base pairs are said to be complementary to one another.

Oligonucleotides and their analogs are also widely used as research reagents. They are useful for the preparation and study of many biological molecules. For example, the use of oligonucleotides and their analogs as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies, and genetic counseling. Commercialization has led to the development of kits which assist individuals untrained in molecular biology to use PCR technology. Oligonucleotides and their analogs, both natural and synthetic, are employed as primers in such PCR technology.

Oligonucleotides and their analogs are also used in other laboratory procedures. Several of these uses are described in common laboratory manuals such as *Molecular Cloning, A Laboratory Manual*, Second Ed., Sambrook et. al., Eds., Cold Spring Harbor Laboratory Press, 1989; and *Current Protocols In Molecular Biology*, Ausubel et. al., Eds., Current Publications, 1993. Such oligonucleotides may be used as synthetic oligonucleotide probes, in screening expression libraries with antibodies and oligomeric compounds, in DNA sequencing, for in vitro amplification of DNA by the polymerase chain reaction, and in site-directed mutagenesis of cloned DNA. See, Book 2 of *Molecular Cloning, A Laboratory Manual*, supra; and "DNA-Protein Interactions and The Polymerase Chain Reaction" in Vol. 2 of *Current Protocols In Molecular Biology*, supra.

Oligonucleotides and their analogs can be tailored for desired uses. Thus a number of chemical modifications have been introduced into oligomeric compounds to increase their usefulness in diagnostics, as research reagents, and as therapeutic entities. Such modifications include those designed to increase binding to a target strand (i.e., increase the melting temperature, Tm), to assist in identification of the oligonucleotide or an oligonucleotide-target complex, to increase cell penetration, to stabilize against nucleases and other enzymes that degrade or interfere with the structure or activity of the oligonucleotides and their analogs, to provide a mode of disruption (terminating event) once the oligonucleotide is sequence-specifically bound to the target, and to improve the pharmacokinetic properties of the oligonucleotide.

Several processes are known for the solid phase synthesis of oligonucleotide compounds. These are generally disclosed in the following United States Patents: U.S. Pat. Nos. 4,458,066, issued Jul. 3, 1984; No. 4,500,707, issued Feb. 19, 1985; and No. 5,132,418, issued Jul. 21, 1992. Additionally, a process for the preparation of oligonucleotides using 2-cyanoethyl phosphoramidite intermediates is disclosed in U.S. Pat. No. 4,973,679, issued Nov. 27, 1990.

A process for the preparation of oligonucleotides using an allylic phosphorus protecting group is disclosed in U.S. Pat. No. 5,026,838, issued Jun. 25, 1991.

The chemical literature discloses numerous processes for coupling nucleosides through phosphorous-containing covalent linkages to produce oligonucleotides of defined sequence. One of the most popular processes is the phosphoramidite technique. See, e.g., Advances in the Synthesis of Oligonucleotides by the Phosphoramidite Approach, Beaucage and Iyer, *Tetrahedron*, 1992, 48, 2223–2311, and references cited therein. A nucleoside or oligonucleotide having a free hydroxyl group is reacted with a protected cyanoethyl phosphoramidite monomer in the presence of a weak acid to form a phosphite-linked structure. Id. Oxidation of the phosphite linkage, followed by hydrolysis of the cyanoethyl group, yields the desired phosphodiester or phosphorothioate linkage. Id.

The cyanoethyl phosphoramidite technique, however, has significant disadvantages. For example, cyanoethyl phosphoramidite monomers are quite expensive. Considerable quantities of monomer remain unreacted in a typical phosphoramidite coupling. Unreacted monomer can be recovered, if at all, only with great difficulty. Moreover, undesired cyanide ion results from these processes. Consequently, there remains a need in the art for synthetic methods that overcome these problems.

One protecting group that has been used as an alternative to the cyanoethyl group is the allyl group. Allyl phosphoramidites, i.e., monomer amidite synthons protected by the allyl group, have been used to prepare oligonucleotides with phosphodiester and phosphorothioate internucleotide linkages. These allyl phosphoramidites are cheaper (allyl alcohol is 10 times cheaper than 2-cyanoethanol on a kilogram basis) to use, and react faster than cyanoethyl phosphoramidites. Oxidation and deblocking procedures, however, have required harsh conditions such as relatively long deprotecting times using mixtures of reagents and elevated temperatures, resulting in poor overall yields. See, Hayakawa et. al., *J. Am. Chem. Soc.*, 1990, 112, 1691–1696 (mixture of tris(dibenzylideneacetone)-dipalladium(0)-chloroform complex, triphenylphosphine, butylamine and formic acid); Hayakawa et al., *Nucleosides & Nucleotides*, 1994, 13, 1337–1345; and Hayakawa et al., *J. Org. Chem.*, 1993, 58, 5551–5555 (mixture of palladium triphenyl-phosphine and triphenylphosphine). Use of zerovalent palladium complexes is inconvenient and limiting for various reasons. Palladium complexes are not practical for use in large-scale synthesis. Further, during synthesis, the palladium catalyst is easily poisoned, resulting in loss of catalytic efficiency. Moreover, traces of Pd(0) remain in the product after the deprotection and purification procedures. This can be lethal when the product is used therapeutically. Also, use of palladium catalyst is tedious and cumbersome.

Deprotection of a TT dimer having an allyl protecting group (3'-O-(allyloxycarbonyl)thymidylyl(3'-5')-thymidine) has been performed using electrochemical means. Hayakawa et. al., *Nucleosides & Nucleotides*, 1998, 17, 441–449. Such methods, however, are not convenient for large-scale synthesis.

The allyl protecting group has also been cleaved by concentrated ammonia at elevated temperatures. Bergmann et. al., *Tetrahedron*, 1995, 51, 6971–6976. This method employs harsh reaction conditions and, therefore, leads to degradation of the product.

These complicated deblocking procedures have discouraged large-scale use of the allyl blocking group in oligonucleotide synthesis.

Accordingly, there is a long-felt need for easier, cheaper and more universally applicable deblocking methods and reagents for removing allyl protecting groups, especially during oligonucleotide synthesis.

SUMMARY OF THE INVENTION

The present invention discloses methods for the preparation of oligomeric compounds having at least one moiety of formula:

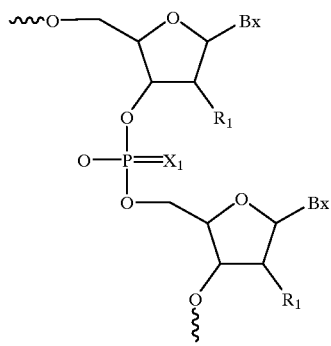

wherein:
$X_1$ is O or S;
Bx is a heterocyclic base moiety; and
$R_1$ is H, a protected hydroxyl group, a 2'-substituent group, or a protected 2'-substituent group;
comprising the steps of:
(a) selecting a compound of formula:

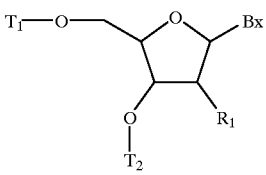

wherein:
Bx is a heterocyclic base moiety; and
$R_1$ is H, a protected hydroxyl group, a 2'-substituent group, or a protected 2'-substituent group;
$T_1$ is an acid labile hydroxyl protecting group; and
$T_2$ is a base labile hydroxyl protecting group or a covalent attachment to a solid support;
(b) deblocking said acid labile hydroxyl protecting group to form a deblocked hydroxyl group;
(c) treating said deblocked hydroxyl group with a further compound having the formula:

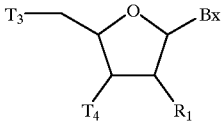

wherein:
Bx is a heterocyclic base moiety; and
$R_1$ is H, a protected hydroxyl group, a 2'-substituent group, or a protected 2'-substituent group;
$T_3$ is a protected hydroxyl group, a nucleoside, a nucleotide, an oligonucleoside or an oligonucleotide; and
$T_4$ is a reactive group for forming an internucleotide linkage;
and an activating agent for a time and under conditions effective to form an extended compound;

(d) treating said extended compound with a capping agent to form a capped compound;
(e) optionally treating said capped compound with an oxidizing agent to form an oxidized compound;
(f) optionally repeating steps (b), (c), (d), and (e) to form a protected oligomeric compound with the proviso that at least one of said $T_4$ has the formula:

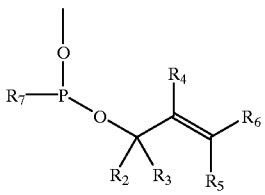

wherein:
each $R_2$, $R_3$ and $R_4$ is, independently, H, $C_1$–$C_6$ alkyl, $C_1$–$C_6$ alkenyl or $C_1$–$C_6$ alkynyl;
each $R_5$ and $R_6$ is, independently, H, $C_1$–$C_6$ alkyl, $C_1$–$C_6$ alkenyl, $C_1$–$C_6$ alkynyl or $C_6$–$C_{14}$ aryl; and
$R_7$ is a leaving group; and
(g) treating said protected oligomeric compound with a solution of concentrated ammonium hydroxide containing a compound of the formula:

wherein:
each $J_1$ and $J_2$ is, independently, H, alkyl, substituted alkyl, aryl, substituted aryl, aralkyl, or substituted aralkyl; wherein said substitutions are amino, halogen, hydroxyl, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, aryl, heterocyclyl, or carbocyclyl;
to form said oligomeric compound.

The method includes attachment of the protected nucleoside to a solid support at the 3'-position. The method also includes the use of —N[—CH(CH$_3$)$_2$]$_2$ as the leaving group. The method further includes the use of 1-H-tetrazole as the activating agent.

In a preferred embodiment of the present invention each $R_5$ and $R_6$ may, independently, be phenyl.

In another preferred embodiment of the present invention the mercapto compound of formula $J_1$—S—$J_2$ is mercaptoethanol, thiocresol, benzyl mercaptan, thiophenol, cysteine, cysteamine, glutathione or dithiothreitol.

In one embodiment of the invention the concentration of the mercapto compound of formula $J_1$—S—$J_2$ is from about 1% to 50%. In a preferred embodiment the concentration is from about 1% to 30%. In a more preferred embodiment the concentration is from about 1% to 10%.

DETAILED DESCRIPTION OF PREFERRED EMBODIMENTS

The present invention provides methods for the preparation of oligomeric compounds having at least one phosphodiester or phosphorothioate internucleoside linkage. Oligomeric compounds of the invention are prepared using a novel deprotection step to form phosphodiester or phosphorothioate internucleoside linkages. The methods utilize an O-allyl phosphorus protecting group on one or all of the internucleoside linkages prior to the deprotection step. This allyl protecting group is cleaved in a deblocking step using an aqueous solution of concentrated ammonium hydroxide having a thiol compound present in the solution.

As used herein, the term "oligomeric compound" refers to compounds containing a plurality of nucleoside monomer subunits that are joined by internucleoside linkages. Preferred internucleoside linkages include phosphorus-containing linkages, such as phosphite, phosphodiester, phosphorothioate, and/or phosphorodithioate linkages. The term "oligomeric compound," therefore, includes naturally-occurring oligonucleotides, their analogs, and synthetic oligonucleotides.

The methods of the present invention are useful for the preparation of oligomeric compounds containing monomeric subunits that are joined by a variety of linkages. In a preferred embodiment of the invention oligomers are synthesized such that all internucleoside linkages bear an allyl protecting group that is amenable to deblocking in a single step with concentrated ammonium hydroxide having a mercapto compound present in the solution.

In some preferred embodiments, a first monomer attached to a solid support is elongated using P—O-allyl monomers or a mixture of P—O-allyl phosphoramidite monomers and other monomers such as β-cyanoethyl phosphoramidite monomers. The methods of the present invention have been used with automated DNA synthesizers to synthesize oligomeric compounds of desired length and sequence. Some oligomeric compounds have been synthesized using only P—O-allyl phosphoramidite monomers. Other oligomeric compounds have been synthesized using P—O-allyl phosphoramidite monomers and β-cyanoethyl phosphoramidite monomers. Table I illustrates selected oligomeric compounds that have been synthesized.

In other preferred embodiments, the methods of the present invention are used in iterative solid phase oligonucleotide synthetic regimes. Representative solid phase techniques are those typically employed for DNA and RNA synthesis utilizing standard phosphoramidite chemistry. See, e.g., Protocols For Oligonucleotides And Analogs, Agrawal, S., Ed., Humana Press, Totowa, N.J., 1993. A preferred synthetic solid phase synthesis utilizes phosphoramidites as activated phosphate compounds. In this technique, a phosphoramidite monomer is reacted with a free hydroxyl group on the growing oligomer chain to produce an intermediate phosphite compound, which is subsequently oxidized to the $P^V$ state using standard methods. This technique is commonly used for the synthesis of several types of linkages, including phosphodiester, phosphorothioate, and phosphorodithioate linkages.

Typically, the first step in such a process is attachment of a first monomer or higher order subunit containing a protected 5'-hydroxyl to a solid support, usually through a linker, using standard methods and procedures known in the art. See, e.g., Oligonucleotides And Analogues A Practical Approach, Ekstein, F. Ed., IRL Press, N.Y., 1991. The support-bound monomer or higher order first synthon is then treated to remove the 5'-protecting group. Typically, this is accomplished by treatment with acid. The solid support-bound monomer is then reacted with a second monomer or higher order synthon having a reactive group for forming an internucleoside linkage. In preferred embodiments the coupling reaction is performed under anhydrous conditions in the presence of an activating agent, such as, for example, 1H-tetrazole, 5-(4-nitrophenyl)-1H-tetrazole, or diisopropylamino tetrazolide.

After the addition of each monomer or higher order synthon a capping step is performed to cap unreacted hydroxyl groups. It is generally preferable to perform a capping step, either prior to or after oxidation or sulfurization of the internucleoside linkage. The capping step is beneficial because it blocks chains that have not reacted in the coupling cycle, thereby preventing the synthesis of shortened oligomers. One representative reagent used for capping is acetic anhydride. Other suitable capping reagents and methodologies can be found in U.S. Pat. No. 4,816,571, issued Mar. 28, 1989, hereby incorporated by reference in its entirety.

Treatment of the growing oligomeric compound with an acid removes the 5'-hydroxyl protecting group enabling participation of the oligomeric compound in another synthetic iteration. The growing oligomeric compound can be extended until an oligomeric compound of desired length is produced.

When the desired oligomeric compound has been synthesized, it is then cleaved from the solid support. The cleavage step can precede or follow deprotection of protected functional groups. During cleavage, the linkages between monomeric subunits are converted from phosphotriester, thiophosphotriester, or dithiophosphotriester linkages to phosphodiester, phosphorothioate, or phosphorodithioate linkages. Linkages having the O-allyl protecting groups are oxidized to the respective phosphodiester or phosphorothioate dependent upon the oxidation reagent used.

Generally, when an allyl protecting group is used in phosphodiester oligonucleotide synthesis, it becomes necessary to use non-standard oxidation conditions. Traditionally, 0.1 M iodine in water/pyridine/THF (2/20/80 v/v/v) is used in automated DNA synthesizers. See, Brown and Brown, in Oligonucleotides and Analogues, Eckstein, F., ed., Oxford University Press, 1991, pp 24. As the allyl group is reactive to iodine/water, a clean oxidation reaction does not occur. As a result, modified non-aqueous oxidation procedures have been developed which employ t-BuOOH. Because non-aqueous t-BuOOH is explosive, its commercial availability has been discontinued. Currently, t-BuOOH is only available as an aqueous solution, use of which compromises the quality of the synthesized product.

To overcome these difficulties, the present invention employs an oxaziridine as a source of oxygen. Phosphite to phosphate oxidation by oxaziridines, while using allyl phosphoramidites, is hitherto unknown. Surprisingly, oxaziridines oxidize phosphites without oxidizing the olefinic bond of the allyl protecting group. Oxaziridines of use in the methods of the present invention include, but are not limited to, 10-camphorsulphonyl oxazaridine, 2-phenylsulphonyl-3-phenyl oxazaridine, 2-(phenyl sulphonyl)-3-(3-nitrophenyl)oxazaridine, 8,8-dihalo-10-camphorsulphonyl oxazaridine, wherein halo is Br, F or Cl. Davis et al., Tetrahedron, 1989, 45, 5703–5742.

The deprotection or removal of the O-allyl protecting group proceeds via an $S_N2'$ substitution reaction with allylic rearrangement. This is carried out using a cocktail solution containing concentrated ammonium hydroxide and a thiol compound (mercapto compound). The thiol group is responsible for allylic substitution followed by elimination of phosphate or thiophosphate group while concentrated ammonium hydroxide deprotects the standard exocyclic amine protecting groups. Nucleophilic attack on the double bond resulting in a shift of the double bond and subsequent release of the phosphodiester or phosphorothioate as illustrated below.

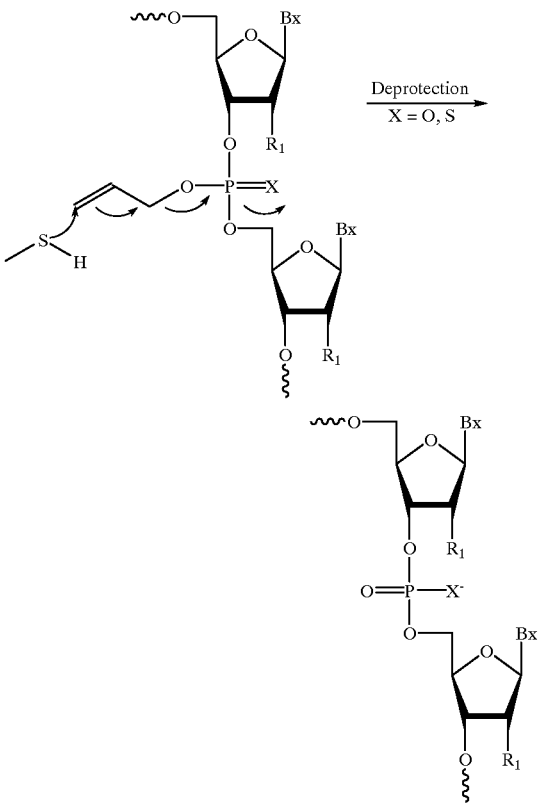

Alternatively, deprotection of olionucleotides, whereby the allyl protecting group is removed, may be carried out as a two step process. The two-step process for deprotection involves: (i) treatment of the allyl group with a solution of a mercapto compound in an aqueous solution of an amine; and (ii) treatment with concentrated ammonium hydroxide. Amines of use in the present invention include, but are not limited to, diethylamine, piperidine, morpholine and DBU.

There is an unexpected increase in the overall yield of oligonucleotides when the allyl blocking group is used. This increase in yield is due, in part, to the use of a mercapto nucleophile in combination with ammonia in the deblocking step. Although not wanting to be bound by theory, it is thought that nucleophilic attack, by the more nucleophilic mercapto compound, on the allylic double bond enhances the overall efficiency of the deblocking step. This enhanced reaction efficiency allows performance of the deblocking step at a lower temperature than has been previously reported.

In one embodiment of the invention the concentration of the mercapto compound in the concentrated ammonium hydroxide solution is from about 1% to about 50%. In a preferred embodiment the concentration of the mercapto compound in the concentrated ammonium hydroxide solution is from about 1 to about 30%. In a more preferred embodiment the concentration of the mercapto compound in the concentrated ammonium hydroxide solution is from about 1 to about 10%.

In a preferred embodiment of the invention the mercapto compound used as the nucleophile in the deblocking step is mercaptoethanol, thiocresol, benzyl mercaptan, thiophenol, cysteine, cysteamine, glutathione or dithiothreitol.

In other preferred embodiments the methods of the invention are used for the preparation of oligomeric compounds, including oligonucleotides and their analogs. As used herein, the term "oligonucleotide" refers to compounds containing a plurality of nucleoside monomer subunits that are joined by internucleoside linkages. Preferred internucleoside linkages include phosphorus-containing linkages such as phosphite, phosphodiester, phosphorothioate and phosphorodithioate linkages. As used herein, the term "oligonucleotide analog" means oligonucleotides and compounds that can contain both naturally-occurring (i.e., "natural") and non-naturally-occurring ("synthetic") moieties, such as nucleosidic subunits containing modified sugar and/or nucleobase portions. Such oligonucleotide analogs are typically structurally distinguishable from, yet functionally interchangeable with, naturally-occurring or synthetic wild type oligonucleotides. Thus, oligonucleotide analogs include all such structures which function effectively to mimic the structure and/or function of a desired RNA or DNA strand, such as hybridizing to a target molecule. The term synthetic nucleoside, for the purpose of the present invention, refers to a modified nucleoside. Representative modifications include modification of a heterocyclic base portion of a nucleoside to give a non-naturally-occurring nucleobase, a sugar portion of a nucleoside, or both simultaneously.

Representative nucleobases or heterocyclic base moieties useful in the compounds and methods described in the present application include, but are not limited to, adenine, guanine, cytosine, uridine, and thymine, as well as other naturally-occurring and non-naturally-occurring nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, and 7-methyl-guanine. Further, naturally and non-naturally-occurring nucleobases include those disclosed in U.S. Pat. No. 3,687,808; by Sanghvi, in *Antisense Research and Application,* S. T. Crooke and B. Lebleu, Eds., Chapter 15, CRC Press, 1993, by Englisch et al., *Angewandte Chemie,* International Edition, 1991, 30, 613. See, especially, pages 622 and 623 of the Englisch et al. reference; *Concise Encyclopedia of Polymer Science and Engineering,* J. I. Kroschwitz, Ed., John Wiley & Sons, 1990, pages 858–859; Cook, *Anti-Cancer Drug Design,* 1991, 6, 585–607.

The term 'nucleosidic base' is further intended to include heterocyclic compounds that can serve as nucleosidic bases including certain 'universal bases' that are not nucleosidic bases in the most classical sense but serve as nucleosidic bases. Especially mentioned as a universal base is 3-nitropyrrole.

Representative 2' sugar modifications (2'-substituent groups) useful in the present invention include fluoro, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs) and PEG-containing groups, such as crown ethers and those which are disclosed by Ouchi et al., *Drug Design and Discovery* 1992, 9, 93; Ravasio et al., *J. Org. Chem.* 1991, 56, 4329; and Delgardo et. al., *Critical Reviews in Therapeutic Drug Carrier Systems* 1992, 9, 249. Further, sugar modifications are disclosed in Cook, *Anti-Cancer Drug Design,* 1991, 6, 585. Fluoro, O-alkyl, O-alkylamino, O-alkyl imidazole, O-alkylaminoalkyl, and alkyl amino substitutions are described in U.S. patent application Ser. No. 08/398,901, filed Mar. 6, 1995, entitled "Oligomeric Compounds having Pyrimidine Nucleotide(s) with 2' and 5' Substitutions."

Additional 2' sugar modifications useful in the present invention include 2'-SR and 2'-NR$_2$ groups, where each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons are disclosed by Hamm et al., *J. Org. Chem.,* 1997, 62, 3415. 2'-NR$_2$ nucleosides are disclosed by Goettingen M., *J. Org. Chem.,* 1996, 61, 6273; and Polushin et al., *Tetrahedron Lett.,* 1996, 37, 3227. Further, additional representative 2'-sugar modifications of use in the present invention include groups having one of the following formula:

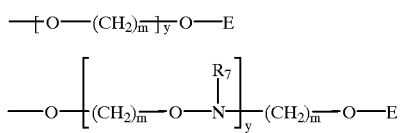

wherein:
m is from 1 to 10;
y is from 0 to 10;
E is N(R$_8$) (R$_9$) or N=C(R$_8$) (R$_9$); and
each R$_7$, R$_8$, and R$_9$ is, independently, H, C$_1$–C$_{10}$ alkyl, a nitrogen protecting group, or R$_1$ and R$_2$ together, are a nitrogen protecting group, or R$_1$ and R$_2$ are joined in a ring structure that includes at least one heteroatom selected from N and O. These 2'-modifications are disclosed in U.S. patent application Ser. No. 09/130,973, filed Aug. 7, 1998, entitled "Aminooxy-Modified Oligonucleotides and Methods for Making Same," hereby incorporated by reference in its entirety.

Representative cyclic 2'-sugar modifications that are of use in the present invention include groups having the formula:

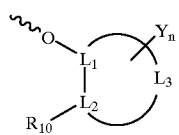

wherein:
L$_1$, L$_2$ and L$_3$ comprise a ring system having from about 4 to about 7 carbon atoms, or having from about 3 to about 6 carbon atoms and 1 or 2 hetero atoms wherein said hetero atoms are selected from oxygen, nitrogen and sulfur, and wherein said ring system is aliphatic, unsaturated aliphatic, aromatic or heterocyclic;
R$_{10}$ is OX$^2$, SX$^2$, N(H)X$^2$ or N(X$^2$)$_2$;
X$^2$ is H, C$_1$–C$_8$ alkyl, C$_1$–C$_8$ haloalkyl, C(=NH)N(H)Z, C(=O)N(H)Z or OC(=O)N(H)Z;
Y$_n$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, N(H)X$^2$, N(X$^2$)$_2$, OX$^2$, halo, SX$^2$ or CN;

n is 0, 1 or 2; and

Z is H or $C_1$–$C_8$ alkyl.

These cyclic 2'-modifications are disclosed in U.S. patent application Ser. No.: 09/123,108, filed Jul. 27, 1998, entitled "RNA Targeted 2'-Modified Oligonucleotides that are Conformationally Preorganized," hereby incorporated by reference in its entirety.

Sugars having O-substitutions on the ribosyl ring are also of use in the present invention. Representative substitutions include, but are not limited to, S, $CH_2$, CHF, and $CF_2$. See, e.g., Secrist et al., *Abstract 21, Program & Abstracts, Tenth International Roundtable, Nucleosides, Nucleotides and their Biological Applications,* Park City, Utah, Sep. 16–20, 1992.

As used herein, the term "alkyl" includes, but is not limited to, straight chain, branched chain, and alicyclic hydrocarbon groups. Alkyl groups of the present invention may be substituted. Representative alkyl substituents are disclosed in U.S. Pat. No. 5,212,295, at column 12, lines 41–50, hereby incorporated by reference in its entirety. As used herein, the term "lower alkyl", is intended to mean alkyl having 6 or fewer carbons.

As used herein, the term "aralkyl" denotes alkyl groups which bear aryl groups, for example, benzyl groups. The term "alkaryl" denotes aryl groups which bear alkyl groups, for example, methylphenyl groups. As used herein, the term "aryl" means aromatic cyclic groups including, but not limited to, phenyl, naphthyl, anthracyl, phenanthryl, and pyrenyl.

As used herein, the term "alkanoyl" has its accustomed meaning as a group of formula —C(=O)-alkyl. A preferred alkanoyl group is the acetyl group.

In general, the term "hetero" means an atom other than carbon, preferably, but not exclusively, N, O, or S. Accordingly, the term "heterocycloalkyl" denotes an alkyl ring system having one or more heteroatoms, i.e., non-carbon atoms. Preferred heterocycloalkyl groups include, for example, morpholino groups. As used herein, the term "heterocycloalkenyl" denotes a ring system having one or more double bonds and one or more heteroatoms. Preferred heterocycloalkenyl groups include, for example, pyrrolidino groups.

In a preferred embodiment of the present invention, oligomer synthesis is performed on an automated synthesizer utilizing a solid support. Solid supports are substrates which are capable of serving as the solid phase in solid phase synthetic methodologies such as those described in U.S. Pat. Nos. 4,415,732; 4,458,066; 4,500,707; 4,668,777; 4,973,679; 5,132,418; 4,725,677 and Re. 34,069.

Linkers are known in the art as short molecules which serve to connect a solid support to functional groups, e.g., hydroxyl groups, of initial synthon molecules in solid phase synthetic techniques. Suitable linkers are disclosed in, for example, *Oligonucleotides And Analogues A Practical Approach,* Ekstein, F.,Ed., IRL Press, N.Y., 1991, Chapter 1, pages 1–23.

Solid supports according to the invention include those generally known in the art to be suitable for use in solid phase methodologies, including, for example, controlled pore glass (CPG), oxalyl-controlled pore glass (Alul et al., *Nucleic Acids Research* 1991, 19, 1527); TentaGel Support; an aminopolyethyleneglycol derivatized support (Wright et al., *Tetrahedron Letters* 1993, 34, 3373); and Poros, a copolymer of polystyrene/divinylbenzene.

In some preferred embodiments of the invention, $T_1$ and $T_2$ are hydroxyl protecting groups and $T_3$ is a protected hydroxyl. A wide variety of hydroxyl protecting groups can be employed in the methods of the invention. Preferably, the protecting group is stable under basic conditions but can be removed under acidic conditions. In general, protecting groups render chemical functionalities inert to specific reaction conditions, and can be appended to and removed from such functionalities in a molecule without substantially damaging the remainder of the molecule. Representative hydroxyl protecting groups are disclosed by Beaucage et al., *Tetrahedron* 1992, 48, 2223–2311, and also in Greene and Wuts, *Protective Groups in Organic Synthesis,* Chapter 2, 2d ed, John Wiley & Sons, New York, 1991. Preferred protecting groups include dimethoxytrityl (DMT), monomethoxytrityl, 9-phenylxanthen-9-yl (Pixyl) and 9-(p-methoxyphenyl)xanthen-9-yl (Mox).

In some preferred embodiments of the invention amino groups are appended to alkyl groups or other groups such as, for example, 2'-alkoxy groups. Such amino groups are also commonly present in naturally-occurring and non-naturally-occurring nucleobases. It is generally preferred that these amino groups be in protected form during the synthesis of oligomeric compounds of the present invention. Representative amino protecting groups suitable for these purposes are discussed in Greene and Wuts, *Protective Groups in Organic Synthesis,* Chapter 7, 2d ed, John Wiley & Sons, New York, 1991. Generally, as used herein, the term "protected" when used in connection with a molecular moiety such as "nucleobase" indicates that the molecular moiety contains one or more functionalities protected by protecting groups.

Sulfurizing agents used during oxidation to form phosphorothioate and phosphorodithioate linkages include Beaucage reagent (Iyer et. al., *J. Chem. Soc.,* 1990, 112, 1253–1254, and Iyer et.al., *J. Org. Chem.,* 1990, 55, 4693–4699); tetraethylthiuram disulfide (Vu and Hirschbein, *Tetrahedron Lett.,* 1991, 32, 3005–3008); dibenzoyl tetrasulfide (Rao et.al., *Tetrahedron Lett.,* 1992, 33, 4839–4842); di(phenylacetyl)disulfide (Kamer, *Tetrahedron Lett.,* 1989, 30, 6757–6760); Bis(O,O-diisopropoxy phosphinothioyl)disulfides (Stec et al., *Tetrahedron Lett.,* 1993, 34, 5317–5320); 3-ethoxy-1,2,4-dithiazoline-5-one (*Nucleic Acids Research,* 1996 24, 1602–1607, and *Nucleic Acids Research,* 1996 24, 3643–3644); Bis(p-chlorobenzenesulfonyl)disulfide (*Nucleic Acids Research,* 1995 23, 4029–4033); sulfur, sulfur in combination with ligands like triaryl, trialkyl, triaralkyl, or trialkaryl phosphines.

In the case of sulfurization, the reaction is performed under anhydrous conditions with the exclusion of air, in particular oxygen, whereas in the case of oxidation, the reaction can be performed under non-aqueous conditions.

In one aspect of the present invention, the compounds of the invention are used to modulate RNA or DNA which code for a protein whose formation or activity is to be modulated. The targeting portion of the composition to be employed is, thus, selected to be complementary to the preselected portion of DNA or RNA. That is, the composition is selected such that it is hybridizable to the preselected portion of the DNA or RNA being targeted.

The methods of the present invention can be used to prepare oligomeric compounds that are used in diagnostics, therapeutics, and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many organelles, e.g., mitochondria and chloroplasts, of eukaryotic cells also include transcription and translation mechanisms. Thus, single cells, cellular populations or organelles can also be included within the definition of organisms that can be treated with therapeutic or diagnostic oligonucleotides.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative, not limiting.

EXAMPLES

Example 1
General Procedures for Oligonucleotide Synthesis

Oligonucleotides were synthesized on a Millipore Expedite™ Nucleic Acid Synthesis System. Solid support resin (~60 mg) was used in each column for 2X1 μmole scale synthesis (dT-CPG and DA-CPG LCA-CPG solid support was purchased from Glen Research). The synthesis protocols used by the automated nucleic acid synthesizer for phosphodiester and phosphorothioate oligonucleotides are shown below. Coupling efficiency was found to be greater than 95% by monitoring the trityl ion released upon deblocking of 5'-OH groups. Modified amidites e.g., adenosine, cytidine, guanosine, and thymidine P—O-allyl amidites were placed in dried vials and dissolved in acetonitrile to a concentration of 100 mg/mL (see Hayakawa, ibid.). Unmodified amidites were placed in dried vials and dissolved in acetonitrile to give 1M solutions. Multiple 1-μmol syntheses were performed for each oligonucleotide. Trityl groups were removed with trichloroacetic acid (975 μL over one minute) followed by an acetonitrile wash.

Phosphodiester Protocol

Unmodified amidites (105 μL, 0.1M) were coupled for 1.5 minutes and allyl amidites (210 μL, 100 mg/mL, 0.08–0.1 M) were coupled for 5 minutes. 1-H-tetrazole in acetonitrile was used as the activating agent. The solid phase was washed with acetonitrile to remove excess amidite. Oxidation was performed using (1S)-(+)-(10-camphorsulfonyl) oxaziridine (CSO, 1.0 g/8.72 mL dry acetonitrile, ~375 μL) with a 3 minute wait step. Unreacted functionalities were capped with a standard capping reagent, e.g., as is available from Millipore (50:50 mixture of tetrahyrdofuran/acetic anhydride and tetrahydrofuran/pyridine/1-methyl imidazole). Coupling efficiency at each step was quantified by monitoring the trityl ion released upon deblocking of 5'-OH groups. The final DMT group was left attached.

Phosphorothioate Protocol

Unmodified amidites (210 μL, 0.1M) were coupled for 1.5 minutes and allyl amidites (210 μL, 100 mg/mL, 0.08–0.1 M) were coupled for 13 minutes. The oxidation step used 3H-1,2-benzodithiole-3-one-1,1-dioxide (225 μL, Beaucage reagent, 3.4 g/200 mL acetonitrile) with one wait step. Unreacted functionalities were capped with a standard capping reagent, e.g., as is available from Millipore (50:50 mixture of tetrahydrofuran/acetic anhydride and tetrahydrofuran/pyridine/1-methyl imidazole). Coupling efficiency at each step was quantified by monitoring the trityl ion released upon deblocking of 5'-OH groups. The final DMT group was left attached.

Deprotection Conditions

Following synthesis oligonucleotides were deprotected using concentrated ammonium hydroxide (2 mL, 30%, aq.) containing 2-mercaptoethanol (2% v/v). Each 1 μM column was treated at 55° C. for approximately 16 hours. Then the volatiles were removed by evaporation using a Savant AS160 Automatic Speed Vac.

Oligonucleotide Purification

After the deprotection step each sample was filtered using a Gelman nylon acrodisc syringe filter (0.45 μM). Each sample is then evaporated using a Savant AS160 automatic speed vac to remove excess concentrated ammonium hydroxide. The crude yield was measured on a Hewlett Packard 8452A Diode Array Spectrophotometer at 260 nm. Crude samples were then analyzed by mass spectrometry (MS) on a Hewlett Packard electrospray mass spectrometer. Trityl-on oligonucleotides were purified by reverse phase preparative high performance liquid chromatography (HPLC). HPLC conditions were as follows: Waters 600E with 991 detector; Waters Delta Pak C4 column (7.8×300 mm); Solvent A: 50 mM triethylammonium acetate (TEA-Ac), pH 7.0; B: 100% acetonitrile; 2.5 mL/minute flow rate; Gradient: 5% B for first five minutes with linear increase in B to 60% during the next 55 minutes. Fractions containing the desired product were collected and evaporated using a speed vac. Oligonucleotides were detritylated in 80% acetic acid for approximately 60 minutes and lyophilized again. Free trityl and excess salt were removed by passing detritylated oligonucleotides through a Sephadex G-25 column and collecting appropriate samples via a Pharmacia LKB SuperFrac fraction collector. The resulting fractions were evaporated using a speed vac. Purified oligos were then analyzed for purity by CGE, HPLC (flow rate: 1.5 mL/min; Waters Delta Pak C4 column, 3.9×300 mm), and MS. The final yield was determined by spectrophotometer at 260 nm.

A dry sample of each oligonucleotide was analyzed by MS, CE, and HPLC. SEQ ID NO: 13 was run through an additional Dowex and Chelex column for NMR studies.

TABLE I

3'-P-O-allyl amidite Derived Oligonucleotides

| SEQ ID NO: | Sequence[1] | Backbone | Mass Calc./ Obs | CE[2]/HPLC[3] retention time |
|---|---|---|---|---|
| 1 | <u>TTT</u> <u>TTT</u> <u>TTT</u> <u>TTT</u> | P=S | 3765.828/ 3764.53 | 3.78/27.01 |
| 2 | <u>TTT</u> <u>TTT</u> <u>TTT</u> <u>TTT</u> | P=O | 3589.828/ 3588.11 | 3.44/19.51 |
| 3 | <u>T</u>GC <u>A</u><u>T</u>C CCC CAG GCC ACC AT | P=S | 6288.688/ 6286.58 | 6.05/22.65 |
| 4 | <u>T</u>GC <u>A</u><u>T</u>C CCC CAG GCC ACC AT | P=O | 5984.688/ 5980.88 | 4.64/17.98 |
| 5 | GA<u>A</u> CT | P=O | 742.589/ | 7.28/19.54 |

TABLE I-continued

3'-P—O-allyl amidite Derived Oligonucleotides

| SEQ ID NO: | Sequence[1] | Backbone | Mass Calc./ Obs | CE[2]/HPLC[3] retention time |
|---|---|---|---|---|
| | | | 742.6 | |
| 6 | GA<u>C</u> CT | P=O | 730.588/ 730.6 | 5.35/8.73 |
| 7 | GA<u>G</u> CT | P=O | 750.590/ 750.6 | 6.77/7.79 |
| 8 | GA<u>A</u> CT | P=S | 774.549/ 774.6 | 6.35/24.65 |
| 9 | GA<u>C</u> CT | P=S | 762.548/ 762.6 | 6.18/24.81 |
| 10 | GA<u>G</u> CT | P=S | 782.550/ 782.7 | 6.23/24.47 |
| 11 | <u>GCC</u> <u>CAA</u> <u>GCT</u> <u>ATC</u> <u>CGT</u> <u>GGC</u> <u>CA</u> | P=O | 6060.550/ 6062.13 | 6.77/22.48 |
| 12 | <u>GCC</u> <u>CAA</u> <u>GCT</u> <u>GGC</u> <u>ATC</u> <u>CGT</u> <u>CA</u> | P=S | 6364.170/ 6365.73 | 6.45/26.95 |
| 13 | <u>GTA</u> <u>C</u>T | P=O | 738.088/ 738.0 | 4.79/17.27 |

[1] All underlined nucleosides (<u>N</u>) were derived from 3'-P—O-allyl phosphoramidite.
[2] Conditions: Capillary gel electrophoresis 9CGE) separations were accomplished with a Beckman P/ACE capillary electrophoresis system (Model MDQ, Beckman, Fullerton, CA) using a 27 cm column with an effective separation length of 20 cm. Gel-filled polyacrylamide columns were prepared using a buffer containing 0.1M Bis-Tris-borate, 8.3M urea (Fluka, New York). Separation was achieved by operating at 40° C. with an applied voltage of 20 or 30 kV. Electropherograms were monitored at 260 nm.
[3] Conditions: Waters 600E with 991 detector; Waters C4 column (3.9 × 300 mm); Solvent A: 50 mM TEA-Ac, pH 7.0; Solvent B: acetonitrile; 1.5 mL/min. flow rate; Gradient: 5% B for first five minutes with linear increase in B to 6% during the next 55 minutes.

Example 2
Deprotection of Oligonucleotide Containing Allyl Protecting Groups Required amounts of allyl phosphoramidites are placed in dry vials. The phosphoramidites are dissolved in acetonitrile and connected to the appropriate ports of a Millipore Expedite™ Nucleic Acid Synthesis System. Approximately 60 mg of solid support resin is used in each column for a 2×1 μmole scale synthesis. The synthesis is run using the diester protocol for phosphodiesters and the thioate protocol for phosphorothioates. Trityl reports indicate coupling results.

After synthesis, oligonucleotides are deprotected on the solid support by treating with 2% 2-mercaptoethanol in 1:1 aqueous piperidine, at room temperature, for approximately 6 hours. The solvent is then evaporated, using a Savant AS160 Automatic SpeedVac, followed by addition of concentrated ammonium hydroxide and deprotection at 55° C. for 12 hours, cooling, and filtering to remove the CPG resin. The reaction mixture is then concentrated and the crude samples are analyzed by MS, HPLC and CE. The crude samples are next purified on a Waters 600E HPLC system with a 991 detector, using a Waters C4 Prep scale column (C4 Prep) under the following conditions:

Solvents: A: 50 mM TEA-Ac, pH 7.0; and B: acetonitrile

Flow Rate: 1.5 mL/min

Gradient: 5% B for the first 5 minutes, followed by linear increase in B to 60% over the next 55 minutes.

After purification, the solvents are evaporated, and the oligonucleotides detritylated with 80% acetic acid at room temperature, for approximately 30 minutes. The solvent is evaporated. The oligonucleotides are next dissolved in concentrated ammonium hydroxide and passed through a column containing Sephadex G-25 using water as the solvent. Fractions are collected using a Pharmacia LKB SuperFrac fraction collector. The resulting purified oligonucleotides are dried and analyzed by MS, HPLC and CE.

Deblocking an allyl protecting group with a mercapto compound results in an increase in the overall yield of the oligomeric compound being synthesized. Moreover, the deblocking reaction of the present invention is simpler and can be carried out under mild conditions as compared to prior art reactions which are more tedious and employ harsh reaction conditions, such as elevated temperatures and concentrated ammonia. An added advantage of using the deblocking procedure of the present invention is that the procedure is amenable to large-scale synthesis of oligomeric compounds.

It is intended that each of the patents, applications, printed publications, and other published documents mentioned or referred to in this specification be herein incorporated by reference in its entirety.

Those skilled in the art will appreciate that numerous changes and modifications may be made to the preferred embodiments of the invention and that such changes and modifications may be made without departing from the spirit of the invention. It is, therefore, intended that the appended claims cover all such equivalent variations as fall within the true spirit and scope of the invention.

What is claimed is:

1. A method of preparing an oligomeric compound having at least one moiety of formula:

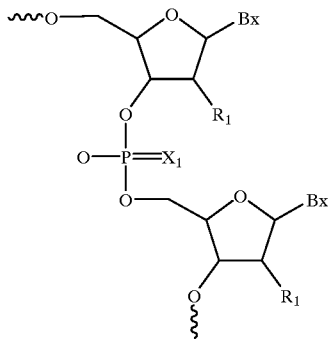

wherein:
- $X_1$ is O or S;
- Bx is a heterocyclic base moiety; and
- $R_1$ is H, a protected hydroxyl group, a 2'-substituent group, or a protected 2'-substituent group; comprising the steps of:
  (a) selecting a compound of formula:

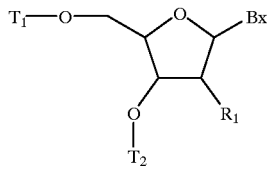

wherein:
- Bx is a heterocyclic base moiety;
- $R_1$ is H, a protected hydroxyl group, a 2'-substituent group, or a protected 2'-substituent group;
- $T_1$ is an acid labile hydroxyl protecting group; and
- $T_2$ is a base labile hydroxyl protecting group or a covalent attachment to a solid support;
  (b) deblocking said acid labile hydroxyl protecting group to form a deblocked hydroxyl group;
  (c) treating said deblocked hydroxyl group with a further compound having the formula:

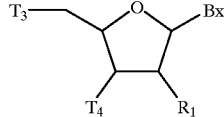

wherein:
- Bx is a heterocyclic base moiety;
- $R_1$ is H, a protected hydroxyl group, a 2'-substituent group, or a protected 2'-substituent group;
- $T_3$ is a protected hydroxyl group, a nucleoside, a nucleotide, an oligonucleoside or an oligonucleotide; and
- $T_4$ is a reactive phosphite group;

and an activating agent for a time and under conditions effective to form an extended compound;
  (d) treating said extended compound with a capping agent to form a capped compound;
  (e) optionally treating said capped compound with an oxidizing agent to form an oxidized intermediate;
  (f) optionally repeating steps (b), (c), (d), and (e) to form a protected oligomeric compound, provided that at least one of said $T_4$ has the formula:

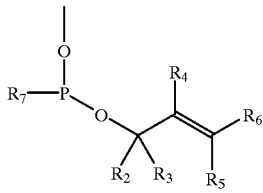

wherein:
- each $R_2$, $R_3$ and $R_4$ is, independently, H, $C_1$–$C_6$ alkyl, $C_1$–$C_6$ alkenyl or $C_1$–$C_6$ alkynyl;
- each $R_5$ and $R_6$ is, independently, H, $C_1$–$C_6$ alkyl, $C_1$–$C_6$ alkenyl, $C_1$–$C_6$ alkynyl or $C_6$–$C_{14}$ aryl; and
- $R_7$ is a leaving group; and
  (g) treating said protected oligomeric compound with a solution of concentrated ammonium hydroxide containing a compound of the formula:

wherein:
- each $J_1$ and $J_2$ is, independently, H, alkyl, substituted alkyl, aryl, substituted aryl, aralkyl, or substituted aralkyl; wherein such substitution can be amino, halogen, hydroxyl, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazolyl, azido, hydrazino, hydroxylamino, isocyanato, aryl, heterocyclyl, or carbocyclyl;
- with the proviso that one of $J_1$ and $J_2$ must be hydrogen;

to form said oligomeric compound.

2. The method of claim 1 wherein said protected nucleoside is attached to a solid support at the 3'-O position.

3. The method of claim 1 wherein said $R_5$ or $R_6$ is phenyl.

4. The method of claim 1 wherein said leaving group is —N{CH(CH$_3$)$_2$}$_2$.

5. The method of claim 1 wherein said activating agent is 1-H-tetrazole.

6. The method of claim 1 wherein said oxidizing agent is an oxaziridine selected from the group consisting of 10-camphorsulphonyl oxazaridine, 2-phenylsulphonyl-3-phenyl oxaziridine, 2-(phenyl sulphonyl)-3-(3-nitrophenyl) oxaziridine, and 8,8-dihalo-10-camphorsulphonyl oxazaridine.

7. The method of claim 1 wherein said compound of formula $J_1$—S—$J_2$ is mercaptoethanol, thiocresol, benzyl mercaptan, thiophenol, cysteine, cysteamine, glutathione or dithiothreitol.

8. The method of claim 1 wherein the concentration of said compound of formula $J_1$—S—$J_2$ in said solution of concentrated ammonium hydroxide is from about 1% to 50%.

9. The method of claim 1 wherein the concentration of said compound of formula $J_1$—S—$J_2$ in said solution of concentrated ammonium hydroxide is from about 1% to 30%.

10. The method of claim 1 wherein the concentration of said compound of formula $J_1$—S—$J_2$ in said solution of concentrated ammonium hydroxide is from about 1% to 10%.

11. The method of claim 1 wherein said step (g) comprises treating said protected oligomeric compound with a mercapto compound and an amine, then treating with concentrated ammonium hydroxide.

12. The method of claim 11 wherein said mercapto compound is of formula:

$$J_1\text{—S—}J_2$$

wherein:
each $J_1$ and $J_2$ is, independently, H, alkyl, substituted alkyl, aryl, substituted aryl, aralkyl, or substituted aralkyl; wherein the substitutions are amino, halogen, hydroxyl, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazolyl, azido, hydrazino, hydroxylamino, isocyanato, aryl, heterocyclyl, or carbocyclyl;

with the proviso that one of $J_1$ and $J_2$ must be hydrogen.

13. The method of claim 12 wherein said compound of formula $J_1$—S—$J_2$ is mercaptoethanol, thiocresol, benzyl mercaptan, thiophenol, cysteine, cysteamine, glutathione or dithiothreitol.

14. The method of claim 11 wherein said amine is diethylamine, piperidine, morpholine or 1,8-diazabicyclo[5.4.0]undec-7-ene (DBU).

15. A method for removing an allyl protecting group from an oligonucleotide comprising contacting said allyl protecting group with a mixture of concentrated ammonium hydroxide and a mercapto compound.

16. The method of claim 15 wherein said mercapto compound is of formula:

$$J_1\text{—S—}J_2$$

wherein:
each $J_1$ and $J_2$ is, independently, H, alkyl, substituted alkyl, aryl, substituted aryl, aralkyl, or substituted aralkyl; wherein the substitutions are amino, halogen, hydroxyl, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazolyl, azido, hydrazino, hydroxylamino, isocyanato, aryl, heterocyclyl, or carbocyclyl with the proviso that one of $J_1$ and $J_2$ must be hydrogen.

17. The method of claim 15 wherein said compound of formula $J_1$—S—$J_2$ is mercaptoethanol, thiocresol, benzyl mercaptan, thiophenol, cysteine, cysteamine, glutathione or dithiothreitol.

18. The method of claim 15 wherein the concentration of said compound of formula $J_1$—S—$J_2$ in said solution of concentrated ammonium hydroxide is from about 1% to 50%.

19. The method of claim 15 wherein the concentration of said compound of formula $J_1$—S—$J_2$ in said solution of concentrated ammonium hydroxide is from about 1% to 30%.

20. The method of claim 15 wherein the concentration of said compound of formula $J_1$—S—$J_2$ in said solution of concentrated ammonium hydroxide is from about 1% to 10%.

21. A method for removing an allyl protecting group from an oligonucleotide comprising contacting said allyl protecting group with a mercapto compound and an amine, then treating with concentrated ammonium hydroxide.

22. The method of claim 21 wherein said mercapto compound is of formula:

$$J_1\text{—S—}J_2$$

wherein:
each $J_1$ and $J_2$ is, independently, H, alkyl, substituted alkyl, aryl, substituted aryl, aralkyl, or substituted aralkyl; wherein the substitutions are amino, halogen, hydroxyl, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazolyl, azido, hydrazino, hydroxylamino, isocyanato, aryl, heterocyclyl, or carbocyclyl with the proviso that one of $J_1$ and $J_2$ must be hydrogen.

23. The method of claim 22 wherein said compound of formula $J_1$—S—$J_2$ is mercaptoethanol, thiocresol, benzyl mercaptan, thiophenol, cysteine, cysteamine, glutathione or dithiothreitol.

24. The method of claim 21 wherein said amine is diethylamine, piperidine, morpholine or 1,8-diazabicyclo[5.4.0]undec-7-ene (DBU).

25. A method for removing an allyl protecting group from an organic compound comprising contacting said allyl protecting group with a mixture of concentrated ammonium hydroxide and a mercapto compound.

26. The method of claim 25 wherein said mercapto compound is of formula:

$$J_1\text{—S—}J_2$$

wherein:
each $J_1$ and $J_2$ is, independently, H, alkyl, substituted alkyl, aryl, substituted aryl, aralkyl, or substituted aralkyl; wherein the substitutions are amino, halogen, hydroxyl, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazolyl, azido, hydrazino, hydroxylamino, isocyanato, aryl, heterocyclyl, or carbocyclyl with the proviso that one of $J_1$ and $J_2$ must be hydrogen.

27. The method of claim 25 wherein said compound of formula $J_1$—S—$J_2$ is mercaptoethanol, thiocresol, benzyl mercaptan, thiophenol, cysteine, cysteamine, glutathione or dithiothreitol.

28. The method of claim 25 wherein the concentration of said compound of formula $J_1$—S—$J_2$ in said solution of concentrated ammonium hydroxide is from about 1% to 50%.

29. The method of claim 25 wherein the concentration of said compound of formula $J_1$—S—$J_2$ in said solution of concentrated ammonium hydroxide is from about 1% to 30%.

30. The method of claim 25 wherein the concentration of said compound of formula $J_1$—S—$J_2$ in said solution of concentrated ammonium hydroxide is from about 1% to 10%.

31. A method for removing an allyl protecting group from an oligonucleotide comprising contacting said allyl protecting group with a mercapto compound and an amine, then treating with concentrated ammonium hydroxide.

32. The method of claim 31 wherein said mercapto compound is of formula:

$J_1$—S—$J_2$ wherein:

each $J_1$ and $J_2$ is, independently, H, alkyl, substituted alkyl, aryl, substituted aryl, aralkyl, or substituted aralkyl; wherein the substitutions are amino, halogen, hydroxyl, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazolyl, azido, hydrazino, hydroxylamino, isocyanato, aryl, heterocyclyl, or carbocyclyl with the proviso that one of $J_1$ and $J_2$ must be hydrogen.

33. The method of claim 32 wherein said compound of formula $J_1$—S—$J_2$ is mercaptoethanol, thiocresol, benzyl mercaptan, thiophenol, cysteine, cysteamine, glutathione or dithiothreitol.

34. The method of claim 31 wherein said amine is diethylamine, piperidine, morpholine or 1,8-diazabicyclo [5.4.0]undec-7-ene (DBU).

* * * * *

UNITED STATES PATENT AND TRADEMARK OFFICE
CERTIFICATE OF CORRECTION

PATENT NO.   : 6,169,177 B1  
DATED        : January 2, 2001  
INVENTOR(S)  : Manoharan Page 1 of 1

It is certified that error appears in the above-identified patent and that said Letters Patent is hereby corrected as shown below:

Title page,
Under References Cited, 4,668,777/Caruthers et al., please delete "5/1987" and insert therefor -- 8/1984 --;

Column 13,
Line 35, please delete "(dT-CPG and DA-CPG LCA-CPG" and insert therefor
-- (dT-CPG and dA-CPG LCA-CPG --;

Column 15,
Line 42, please delete "6%" and insert therefor -- 60% --;

Signed and Sealed this

Seventh Day of May, 2002

Attest:

Attesting Officer

JAMES E. ROGAN
Director of the United States Patent and Trademark Office